United States Patent [19]  
Druliner et al.

[11] 4,326,084
[45] Apr. 20, 1982

[54] PROCESS FOR PRODUCING A MIXTURE CONTAINING CYCLOHEXANOL AND CYCLOHEXANONE FROM CYCLOHEXANE

[75] Inventors: Joe D. Druliner, Newark; Steven D. Ittel, Wilmington; Paul J. Krusic, Wilmington; Chadwick A. Tolman, Wilmington, all of Del.

[73] Assignee: E. I. Du Pont de Nemours and Company, Wilmington, Del.

[21] Appl. No.: 184,635

[22] Filed: Sep. 16, 1980

Related U.S. Application Data

[63] Continuation-in-part of Ser. No. 83,644, Oct. 11, 1979.

[51] Int. Cl.$^3$ .................. C07C 27/12; C07C 29/50; C07C 45/33
[52] U.S. Cl. .................. 568/360; 568/836; 252/431 N
[58] Field of Search .......... 568/360, 342, 836; 252/431 N

[56] References Cited

U.S. PATENT DOCUMENTS

| | | | |
|---|---|---|---|
| 2,851,496 | 9/1958 | Cates et al. | 568/342 |
| 3,530,185 | 9/1970 | Pugi | 568/358 |
| 3,917,708 | 11/1975 | Kuessner et al. | 568/342 |
| 3,923,895 | 12/1975 | Costantini et al. | 568/342 |
| 3,925,316 | 12/1975 | Brunie et al. | 568/342 |
| 3,927,105 | 12/1975 | Brunie et al. | 568/358 |
| 3,957,876 | 5/1976 | Rapoport et al. | 568/358 |
| 3,987,100 | 10/1976 | Barnette et al. | 568/358 |
| 4,034,047 | 7/1977 | Angstadt | 568/836 |
| 4,243,551 | 1/1981 | Ward | 252/431 N |

OTHER PUBLICATIONS

Siegl, J. Org. Chem., vol. 42(11), pp. 1872–1878 (1977).
Robinson et al, Inorg. Chem., vol. 6(2), pp. 392–394 (1967).
Semenchenko et al, Russ. J. Phys. Chem., 47, 654 (1973).
Hock et al, J. Prakt. Chem., 9, 173 (1959).
Kamiya, Chem. Abstr., 72, 11790y (1970).
Ochiai, Tetrahedron, 20, 1819 (1964).

*Primary Examiner*—Natalie Trousof
*Assistant Examiner*—James H. Reamer

[57] ABSTRACT

There is disclosed an improved process for oxidizing cyclohexane to produce a reaction mixture containing cyclohexyl hydroperoxide and decomposing the cyclohexyl hydroperoxide to form a mixture containing cyclohexanone and cyclohexanol comprising using in the oxidation step and/or the decomposition step as a catalyst a transitional metal complex of certain 1,3-bis(pyridylimino)isoindolines.

23 Claims, 8 Drawing Figures

PROCESS FOR PRODUCING A MIXTURE CONTAINING CYCLOHEXANOL AND CYCLOHEXANONE FROM CYCLOHEXANE

CROSS-REFERENCE TO RELATED APPLICATION

This application is a continuation-in-part of U.S. application Ser. No. 083,644 filed on Oct. 11, 1979.

BACKGROUND OF THE INVENTION

1. Field of the Invention

This invention relates to an improved process for producing a mixture containing cyclohexanol and cyclohexanone.

More particularly, the invention relates to an improved catalytic process for production of a mixture containing cyclohexanol and cyclohexanone wherein cyclohexane is oxidized in air to produce a reaction mixture containing cyclohexyl hydroperoxide (CHHP) and the cyclohexyl hydroperoxide is decomposed.

The principle products of the decomposition, cyclohexanone and cyclohexanol, are readily converted by oxidation to adipic acid. Adipic acid is used in large volume in the preparation of condensation polymers, particularly polyamides.

2. Description of the Prior Art

The oxidation of cyclohexane to mixtures containing cyclohexanes and cyclohexanol is a well-known, competitive, large-volume industrial process. The product is frequently referred to as K/A (Ketone-Alcohol) mixture. Experience in the operation of the process, which is reflected in the disclosures of many patents, has taught that the oxidation must be carried out at low conversion, if it is desired to maximize the yield of K and A and minimize the formation of other oxidation products, some of which have deleterious effects in the production of adipic acid and/or on the purity of the adipic acid produced. Relatively minor process improvements, such as in the yield of K and A, can result in highly beneficial cost advantage. There is, therefore, a strong economic incentive to increase the efficiency of the oxidation process.

U.S. Pat. No. 2,851,496 issued to Gates et al on Sept. 9, 1958 discloses a process comprising the oxidation of cyclohexane with molecular oxygen optionally in the presence of a catalyst to obtain a mixture containing cyclohexanol, cyclohexanone and cyclohexyl hydroperoxide and heating said mixture in the presence of a bed of solid peroxide decomposition catalyst to decompose the CHHP.

U.S. Pat. No. 3,530,185 issued to Pugi on Sept. 22, 1970 discloses a process for preparing partial oxidation products of cyclohexane which includes contacting at elevated temperature and pressure a stream of liquid cyclohexane at each of several successive stages of an oxidation zone with a mixture of gases including molecular oxygen at controlled partial pressure and inert gas. The patent discloses that a catalyst, such as a cobalt compound, can be present during the oxidation, and will cause cyclohexyl hydroperoxide formed during said oxidation to decompose.

U.S. Pat. No. 3,957,876 issued to Rapoport et al on May 18, 1976 discloses a process for oxidation of cyclohexane to produce a product fluid consisting essentially of unreacted cyclohexane, cyclohexanone, cyclohexanol and greater than 15% of cyclohexyl hydroperoxide by weight based on total products, consisting essentially of passing a fluid containing cyclohexane and a cyclohexane soluble cobalt salt, such as cobalt naphthenate, cobalt octoate, cobalt laurate, cobalt palmitate, cobalt stearate, cobalt linoleate or cobalt acetylacetonate, in the amount of 0.1 to 5 parts per million parts of product fluid through a series of oxidizing zones while contacting the fluid with a gas containing molecular oxygen.

U.S. Pat. No. 3,987,100 issued to Barnette et al on Oct. 19, 1976 discloses cyclohexane oxidation in the presence of a binary catalyst system comprising specific amounts of chromium and cobalt, reacting any cyclohexyl hydroperoxide that may be formed in the presence of said binary catalyst system, and recovering a product of cyclohexanone and cyclohexanol in a specified ratio.

An important step in the rather complicated overall oxidation process is the decomposition of cyclohexyl hydroperoxide (CHHP), which is a primary oxidation product of cyclohexane. See for example U.S. Pat. Nos. 2,851,496, 3,923,895, 3,925,316, and 3,927,105. Since the efficiency of this decomposition step contributes to the efficiency of the overall oxidation process, improvements in the decomposition of CHHP are a desirable objective.

Depending on process conditions, the decomposition of CHHP can take place in a number of ways.

CHHP can decompose "by itself," in which case all the cyclic $C_6$ moieties in the K and/or A produced come directly from CHHP.

In the presence of cyclohexane, CHHP also decomposes by a reaction involving the cyclohexane, and some of the cyclohexane is converted to K and/or A. This mode of decomposition is discussed in U.S. Pat. No. 2,851,496 and is also referred to in U.S. Pat. Nos. 3,957,876 and 3,987,100. U.S. Pat. No. 2,851,496 represents this process as being the reaction of one mole of cyclohexane with one mole of CHHP to give two moles of A. In the present work, however, the reaction has been found to yield both K and A, as reported in U.S. Pat. No. 3,987,100. This involvement of cyclohexane in the production of K and A is referred to herein as "cyclohexane participation."

Cyclohexane participation results in a higher conversion of cyclohexane to useful oxidation products than would be realized if the CHHP decomposed by itself. It would be of great advantage to increase the amount of K and A derived from cyclohexane via cyclohexane participation without lowering the yield of K and A derived directly from CHHP.

Semenchenko et al, *Russ. J. Phys. Chem.* 47 (5), 654, (1973) have found that the decomposition of CHHP in cyclohexane in the presence of cobalt stearate is initially rapid and then slows down, i.e., the activity of the catalyst falls rapidly as the hydroperoxide decomposes.

Certain cobalt complexes with anionic heterocyclic nitrogen-donor ligands apparently catalyze the decomposition of other organic hydroperoxides. For example, Hock and Kropf, *J. Prakt. Chem.* 9, 173, (1959) tested the phthalocyanine derivatives of seven different metals as catalysts for the autoxidation of cumene (isopropylbenzene). They found that cobalt phthalocyanine gave the highest overall conversion of cumene to oxidation products, the highest conversion of cumene to K/A mixture, and the lowest conversion to cumene hydroperoxide in the final product mixture. Since the ketone and alcohol (acetophenone and 2-phenyl-2-propanol) are known to be decomposition products of the hydroperoxide, it can be inferred that the cobalt compound was the best catalyst for the decomposition of the hydroperoxide. The amount of hydroperoxide in the final product mixture was small but significant, and corresponded to 5.8% of the cumene originally charged.

Kamiya, *Kogyo Kagaku Zasshi* 72 (8), 1693, (1969); *Chem. Abstr.* 72, 11793Y, (1970) reports that cobalt phthalocyanine was a better catalyst than cobalt dodecanoate in the oxidation of cumene, and for the autoxidation of ethylbenzene. In each case the activity was "due to the decomposition of hydroperoxides."

Ochiai, *Tetrahedron* 20, 1819, (1964) studied the mechanisms by which transition metal stearates and transition metal phthalocyanines, including those of cobalt, participate in the autoxidation of cyclohexene. The author concluded that cobalt stearate decomposed the intermediate hdyroperoxide to form free radicals, and suggested that cobalt phthalocyanine was "liable" to decompose the hydroperoxide and undergo decomposition itself at the same time. The nature of the final products and the relative efficiencies of cobalt stearate and cobalt phthalocyanine are not reported.

In summary, improvements in the oxidation step and/or the decomposition step of the process for making from cyclohexane a mixture containing cyclohexanol and cyclohexanone are highly desirable objectives.

SUMMARY OF THE INVENTION

The present invention provides an improvement in the process for producing a mixture containing cyclohexanol and cyclohexanone wherein cyclohexane is oxidized in air to provide a reaction mixture containing cyclohexyl hydroperoxide and the cyclohexyl hydroperoxide is decomposed in the presence of starting cyclohexane to provide a mixture containing cyclohexanol and cyclohexanone. The improvement comprises (1) conducting the oxidation step by contacting cyclohexane with air at a temperature of from about 120°–160° C. in the presence of a catalytic amount of catalyst composition consisting essentially of at least one transition metal complex having the structural formula

I wherein the primary ligand is the entity in brackets;
M is Co, Mn or Fe;
$R^1$, $R^2$, $R^3$, $R^4$, $R^5$, and $R^6$ are independently hydrogen, lower alkyl, lower alkoxyalkyl, phenyl, benzyl, or phenethyl or any two adjacent members of $R^1$ through $R^6$ are jointly four CH entities of a benzene ring fused to the pyridine ring;
$R^7$, $R^8$, $R^9$ and $R^{10}$ are independently hydrogen, lower alkyl or lower alkoxyalkyl or any two adjacent members of $R^7$ through $R^{10}$ can jointly be four CH entities of a benzene ring fused to the benzene ring of the isoindoline moiety;
X is an ancillary anionic ligand;
n is 1 or 2;
p is 0, 1 or 2, provided that n+p is 2 or 3;
with the proviso that when there are two primary ligands the values of $R^1$ through $R^{10}$ can be different for each ligand and when there are two ancillary anionic ligands the value of X can be different; and/or (2) conducting the decomposition step by contacting a reaction mixture containing cyclohexane and from about 0.1 to about 10% by weight of cyclohexyl hydroperoxide with a catalytic amount of said catalyst composition at a temperature of from about 80°–160° C., optionally in the presence of molecular oxygen.

The advantages that accrue from using such a catalyst, relative to the results obtained with the cobalt(II) salt of a fatty acid such as cobalt 2-ethylhexanoate, include the following:

(1) longer catalyst life
(2) higher conversions of CHHP to K and A
(3) operability at lower temperatures (80°–160° C.)
(4) reduced formation of insoluble metal-containing solids.

DETAILED DESCRIPTION OF THE INVENTION

The compounds used as catalyst in the process of the invention as represented by the formula previously set forth herein are transition metal derivatives of certain 1,3-bis(pyridylimino)isoindolines. Alternatively, the compounds can be represented by formula A wherein $R^1$ through $R^{10}$, X, M, p and n are as previously defined.

As used herein "lower alkyl" means alkyl of 1–6 carbon atoms. The preferred values of $R^1$ through $R^6$ are hydrogen, methyl and t-butyl. Due to availability of starting materials, preferably at least one of $R^1$, $R^2$ and $R^3$ and at least one of $R^4$, $R^5$ and $R^6$ are hydrogen; and more preferably at least two of each set of these R groups are hydrogen. Most preferably at least one of each set of these R groups is methyl or $R^2$ and $R^5$ are t-butyl and the other of these R groups are hydrogen.

Again due to availability of starting materials, $R^7$ through $R^{10}$ are preferably hydrogen, methyl or t-butyl; p is preferably 0 or 1; and n is preferably 2. Preferably M is Co, Mn or Fe and most preferably M is Co.

The ancillary anionic ligand, X, can be selected from various possibilities which include carboxylate groups, such as acetate, propionate, 2-ethylhexanoate, gluconate and naphthenate; an anion of any other organic acid; hydroxide and $\mu$-oxide ($O^{-2}/2$). Preferably X is a carboxylate group. The nature of the ancillary anionic ligand has little direct effect on catalyst activity but may affect solubility and, thus, indirectly activity.

Examples of catalyst of the invention are the cobalt-(II), manganese(II) and iron(II) derivatives of 1,3-bis(2-pyridylimino)isoindoline, the cobalt derivative being formulated here in abbreviated form as $Co(BPI)_2$; and the cobalt, manganese and iron derivatives of 1,3-bis(3-methyl-2-pyridylimino)isoindoline, 1,3-bis(3,4-dimethyl-2-pyridylimino)isoindoline, 1,3-bis(3-ethyl-2-pyridylimino)isoindoline, 1,3-bis(3-butyl-2-pyridylimino)isoindoline, 1,3-bis(4-pentyl-2-pyridylimino)isoindoline, 1,3-bis(4-isohexyl-2-pyridylimino)isoindoline, 1,3-bis(5-phenyl-2-pyridylimino)isoindoline, 5-t-butyl-1,3-bis(2-pyridylimino)isoindoline), 4,7-dimethyl-1,3-bis(3-methyl-2-pyridylimino)isoindoline, 4,5,6-trimethyl-1,3-bis(2-pyridylimino)isoindoline, 4,5,6,7-tetrakis(t-pentyl)-1,3-bis(2-pyridylimino)isoindoline, 4-hexyl-1,3-bis(2-pyridylimino)isoindoline, and 1,3-bis(1-isoquinolylimino)isoindoline. The most preferred catalysts, because of availability and activity, are $Co(BPI)_2$, the cobalt derivative of 1,3-bis(3-methyl-2-pyridylimino)isoindoline [$Co(3MeBPI)_2$], and a mixture of cobalt(II) derivatives of bis(monomethyl-2-pyridylimino)isoindolines made from a mixture of 2-amino-3-, 4- and 5-methylpyridines as one of the starting materials.

Preparation of Catalysts

The catalysts of the invention can be made by literature methods or improvements thereof.

1,3-Bis(pyridylimino)isoindolines can be made by the method of Siegl, *J. Org. Chem.*, 42 (11), 1872 (1977). For the purposes of the present invention, 1,3-bis(pyridylimino)isoindoline can be prepared by using calcium chloride in the method described in the section entitled "General Preparation . . . Using Alkaline Earth Salts" (page 1877 of the Siegl article).

The preparation of transition metal(II) derivatives of 1,3-bis(pyridylimino)isoindolines is described by Robinson et al, *Inorg. Chem.*, 6 (2), 392 (1967). For the purposes of the present invention, the cobalt derivatives can be made by the following modification of this literature method:

The 1,3-bis(pyridylimino)isoindoline, sodium hydroxide, and methanol are stirred in proper proportions until the sodium hydroxide dissolves. Heat can be applied to speed the dissolution. A solution of cobalt(II) chloride hexahydrate in the minimum amount of methanol is then added with stirring, whereupon the cobalt derivative precipitates as a deep-red solid. The mixture is stirred for 15 minutes, and the product is separated by filtration, washed with ether, and dried under reduced pressure to produce the cobalt(II) derivative of 1,3-bis(2-pyridylimino)isoindoline, $Co(BPI)_2$.

To avoid traces of halide in the catalyst, a transition metal salt other than a halide is advantageously used as the starting material.

Transition metal derivatives of 1,3-bis(2-pyridylimino)isoindolines can also be prepared by the one-step method described in copending U.S. application Ser. No. 187,719. In this process the appropriate phthalonitrile, the appropriate 2-aminopyridine, and the transition metal carbonate are reacted, optionally in the presence of an alkaline earth metal carbonate, to give the desired transition metal derivative directly.

Catalyst compositions containing a transition metal derivative of a 1,3-bis(pyridylimino)isoindoline can also be made in situ by mixing from about one to about two equivalents of the 1,3-bis(pyridylimino)isoindoline with a transition metal(II) salt having an anion X as previously defined. The salt preferably is a transition metal-(II) carboxylate such as the acetate, propionate, 2-ethylhexanoate, stearate, naphthenate or gluconate. The transition metal salt can also be, for example, an organic phosphate, sulfate, or sulfonate like those of U.S. Pat. No. 3,917,708. The desired 1,3-bis(pyridylimino)isoindoline is conveniently added as a solution in a suitable solvent such as benzene, chlorobenzene, or cyclohexane. When about one equivalent of the 1,3-bis(pyridylimino)isoindoline compound is used, there is probably an appreciable concentration of the compound MLX, where the L is the anion of the particular 1,3-bis(pyridylimino)isoindoline and X is the anion of the added transition metal salt. These compounds are also catalysts for the process of the invention.

If desired, compounds of the type MLX can be made and isolated by a method described by Siegl, *J. Org. Chem.*, 42 (11), 1872 (1977).

Catalyst compositions of the invention can also be prepared by a one-step method in which a metal salt, usually a metal carboxylate, such as 2-ethylhexanoate, is reacted with a phthalonitrile and a 2-aminopyridine, optionally in the presence of an alkaline earth metal carbonate.

Mixed-metal catalyst compositions of the invention, in which there are at least two transition metal derivatives of formula I involving at least two different metals, can be prepared by any of the foregoing methods using a mixture of at least two transition metal compounds as starting materials. Alternatively, mixed-metal catalyst compositions can be made by intimately mixing two or more transition metal complexes of formula I.

Catalyst compositions that are mixtures of complexes of formula I having ligands which are different isomerically or otherwise can be made by modifications of the foregoing methods in which mixtures of the 1,3-bis(2-pyridylimino)isoindoline starting compounds or precursors thereto are used. For example, isomer mixtures of cobalt(II) derivatives of 1,3-bis(2-pyridylimino)isoindolines in which one of $R^1$, $R^2$, and $R^3$ and one of $R^4$, $R^5$, and $R^6$ are methyl and the other four R's are hydrogen can be made by using a mixture of 1,3-bis(3-methyl-2-pyridylimino)isoindoline, 1,3-bis(4-methyl-2-pyridylimino)isoindoline and 1,3-bis(5-methyl-2-pyridylimino)isoindoline. This composition is herein designated $Co(345MEBPI)_2$. Catalyst compositions of this kind can also be prepared by either of the one-step methods previously described by using a mixture of 2-aminopyridines, e.g., a mixture of 2-amino-3-, 4-, and 5-methylpyridines, as one of the starting materials.

Catalyst compositions of the invention wherein the transition metal is in the trivalent state can be prepared by electrochemical oxidation of the neutral divalent derivative of formula I. Alternatively, trivalent transition metal derivatives of formula I can be prepared by oxidizing the corresponding divalent derivatives, $ML_2$, with peracids which would give directly a complex of the formula $ML_2X$ where M, L and X are as previously defined. For example, oxidation of a cobalt derivative of formula I, wherein n is 2 and p is 0, with peracetic acid or perbenzoic acid would give $CoL_2$(acetate) or $CoL_2$(benzoate), respectively. Also, complexes of this kind can be prepared by oxidizing the divalent complex, $ML_2$, with bromine to obtain a derivative of the type $ML_2Br$. Then, the derivative $ML_2Br$ can be subjected to a metathesis reaction with an alkali metal salt of the desired organic acid to yield a $ML_2X$ complex. For example, $Co(3MeBPI)_2$ can be oxidized with bromine to give $Co(3MeBPI)_2Br$ which can be subjected to metathesis with sodium acetate to obtain $Co(3MeBPI)_2$(acetate).

Process Variables

Oxidation

As mentioned earlier herein, processes for the oxidation of cyclohexane are well described in the literature. The present invention can be used in the oxidation process regardless of whether cyclohexane oxidation and CHHP decomposition are conducted in separate stages or in the same stage and regardless of whether or not the oxidation is conducted in multizones. It is to be understood that except for the details given here the oxidation and decomposition steps are conducted as described in the literature.

The distribution of products from the oxidation of cyclohexane depends upon both temperature and percent conversion of the cyclohexane to products. The lower temperature oxidation made possible by the process of the invention can be utilized in two ways depending on whether it is desired to produce primarily cyclohexanone and cyclohexanol or primarily adipic acid. The maximum yield of cyclohexanone and cyclohexanol is realized at the lowest possible temperature and at conversions below 4%. However, conversions lower than about 2% are not economical because of the large energy input required for recycling unreacted cyclohexane. The maximum yield of adipic acid and its precursors, such as 1,2-cyclohexanediol, is achieved at higher conversions because they arise largely by further oxidation of cyclohexanol and cyclohexanone. At these higher conversions, low-temperature oxidation favors a high proportion of adipic acid with a reduction in the less commercially valuable monobasic acids.

Optimum conditions depend on factors, such as the particular catalyst, conversion desired, and time. In the process of the invention, oxidation of cyclohexane can be conducted at a temperature of about 120°–160° C. Preferably the temperature is about 140°–150° C. since the best compromise between yield and rate is obtained at this temperature range. A catalyst concentration of from about 0.1–10 ppm of metal by weight in the total mixture is preferred, depending on the temperature and conversion desired. Pressures of from about 30–350 psi (210–2410 kPa) gauge pressure can be employed.

Decomposition of CHHP

To moderate the reaction, the process is usually carried out in a suitable solvent. Suitable solvents include alkanes, such a hexane, heptane, and isooctane; cycloalkanes, such as cyclopentane, methylcyclopentane, and cyclohexane; aromatic hydrocarbons, such as benzene, toluene, and xylene; and mixtures of such hydrocarbons with ethers such as diethyl ether. Since CHHP is usually produced industrially as a solution in cyclohexane from the oxidation of cyclohexane, a convenient and preferred medium for the reaction is cyclohexane. Such a solution can be used as received from the first step of the cyclohexane-oxidation process or after removal of some of the constituents by known processes.

The concentration of CHHP in the reaction mixture is from about 0.1% to about 10% by weight and preferably from about 0.5% to about 3% by weight based on the total reaction mixture. The catalyst concentration in the total mixture is from about 0.1 to about 30 ppm of metal, and preferably from about 0.1 to 5 ppm. Usually lower catalyst concentrations will be required at higher temperatures. The time will depend on the temperature and the catalyst concentration and will usually be from about 5 to about 30 minutes. Longer times can be used, but usually no advantage results. As shown in the examples, the progress of the CHHP decomposition can be followed photometrically and calorimetrically. These methods are helpful in determining the optimum process time for a given catalyst and a particular set of concentration/temperature variables. Generally the temperature used in the decomposition step of the present invention will be from about 80° to 160° C. with from 100° to 130° C. being the preferred temperature range. Pressures of from about 10–200 psi (69–1380 kPa) gauge pressure can be used.

In commercial operation, as noted in the teachings of the many patents in this field, CHHP and cyclohexane will be supplied to the CHHP decomposition reactor as the liquid effluent from the primary oxidation zone; this solution will also contain cyclohexanone and cyclohexanol, along with minor amounts of other oxidation products and any catalyst remaining from the oxidation step. However, a solution of pure CHHP and cyclohexane can also be used as the starting material for the decomposition step.

In the process of the invention decomposition of CHHP can be conducted in the presence or absence of molecular oxygen. As an additional feature of the present invention, it has been found that when CHHP is decomposed in a stage separate from oxidation and at a lower temperature, the yield of cyclohexanone and cyclohexanol from cyclohexane participation in the decomposition of CHHP can be increased, without significantly reducing the yield of cyclohexanone and cyclohexanol obtained directly from CHHP, simply by adding molecular oxygen to the decomposition reaction mixture.

Oxygen is generally used as a mixture with an inert gas such as nitrogen or argon. For example, depending on the concentration of oxygen desired, the latter can be supplied as air, as air enriched with added oxygen, or as air diluted with additional nitrogen. Straight air is a convenient and preferred source.

Any amount of added oxygen will bring about increased production of cyclohexanone and cyclohexanol via cyclohexane participation. Usually the oxygen/CHHP mole ratio will be from about 0.1 and 10. Significant increases begin to occur when the ratio is about 0.5. The increase rises as the oxygen/CHHP ratio is raised and depends to some extent on the nature and concentration of the catalyst. The preferred range of oxygen/CHHP mole ratios is from about 0.5 to about 3.0. Higher ratios can be used but confer no advantage.

The concentration of CHHP in the reaction mixture is generally from about 0.1% and 10% by weight and preferably between about 0.5% and 3% by weight. The catalyst concentration will be as previously given.

The time required for the process step of decomposition in the presence of molecular oxygen in a batch operation, or the residence time in a continuous operation, will of course depend in part on the CHHP concentration, the catalyst and its concentration, the oxygen/CHHP mole ratio, and the temperature. Usually the reaction time will be between 10 minutes and 60 minutes, and preferably between 10 minutes and 30 minutes. When oxygen is used during the decomposition step the temperature will be from about 80° to 140° C., and more preferably, from about 100°–120° C.

The present invention can be operated by performing the oxidation and decomposition steps concurrently in the same stage or the oxidation and decomposition can be performed in separate stages. The process of the invention can be performed by a batch method or a continuous method. It is preferred to operate the process of the invention in a continuous mode either using uncatalyzed oxidation at about 165° C. and CHHP decomposition in the presence of molecular oxygen using a temperature of from about 100°–130° C. or using oxidation in the presence of the catalyst of the invention at 130°–150° C., optionally followed by decomposition as described above.

The invention is further illustrated by the following examples in which all temperatures are in degrees Centigrade and all percentages are by weight unless otherwise specified.

EXAMPLES

The apparatus used in Examples 1–7 was a stainless-steel pulse reactor having a volume of about 270 ml and usable at internal pressures up to about 15 psi (103 kPa) gauge pressure. The apparatus had a pressure-relief valve to insure that allowable pressure was not exceeded and was equipped with a side-arm with a septum for injection of liquid from a hypodermic syringe. Liquid contents (usually about 60 ml) in the apparatus could be stirred by an external magnetic drive. The inside walls and stirring paddle were coated with Teflon ® fluorocarbon resin to prevent CHHP decomposition on the metal surfaces. Heating was provided by partial immersion in an oil bath regulated by a proportional heater control. Temperatures were measured with a platinum resistance thermometer using digital temperature display and analog output.

The reactor was also equipped with a side-arm light probe for observing chemiluminescence produced during CHHP decomposition. The light thus produced passed through a glass rod in the side-arm and through a flexible light guide to a photomultiplier (PM). The current output from the photomultiplier (typically 0.1–100 nA) was converted to a voltage by an electrometer amplifier with good linearity and low noise characteristics. Voltages representing the temperature (T) and the chemiluminescent light intensity (I) were passed through an analog/digital converter and stored on disks and magnetic tapes in a computer system.

EXAMPLE 1

Procedure

In an atmosphere of air, the reactor described above was charged with 5.4 mg of Co(BPI)$_2$, 60 cc of cyclohexane, and 0.6 cc of an 0.1 M solution of 9,10-dibromoanthracene (DBA) in chlorobenzene to obtain a resulting mixture which contained 10 ppm of cobalt by weight. The DBA served as a light enhancer. The Co(BPI)$_2$ was washed into the reactor with the cyclohexane. Stirring at about 1000 rpm was started and was continued throughout the run. The mixture was heated to about 99°, at which temperature data collection was started by the computer system, data points for both I and T being stored every two seconds. The photomultiplier shutter was initially closed. After data had been collected for 20 seconds, the shutter was opened, and 30 seconds thereafter (50 seconds after the start of data collection) 0.6 cc of a 60% solution of CHHP in diethyl ether was injected by syringe. Ten minutes after this addition 0.7 cc of trimethyl phosphite (more than enough to react with the CHHP) was injected by syringe to quench any remaining CHHP. Stirring at about 99° was continued for 10 minutes more, after which data collection was stopped and the mixture was cooled to room temperature. A portion of the mixture was filtered through an 0.5-$\mu$m filter; analysis by atomic absorption showed that the filtrate contained 2.2 ppm of cobalt.

Figure 1:
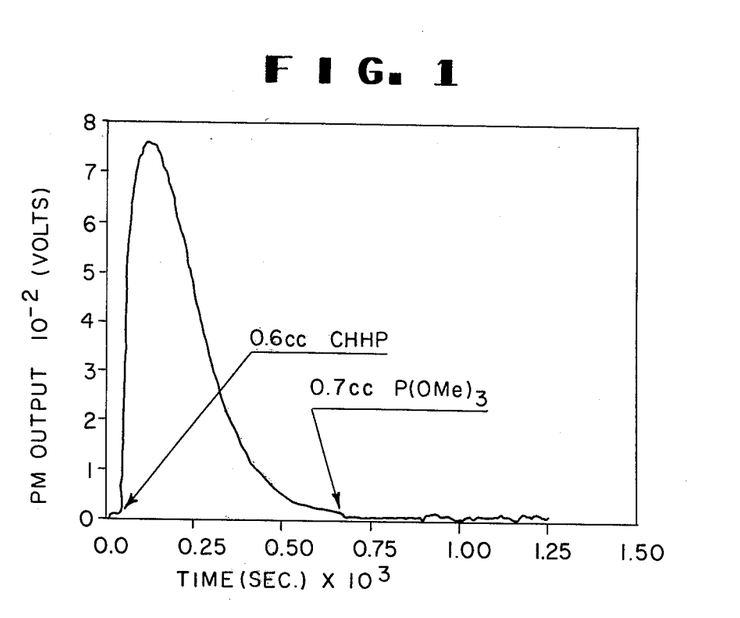
Figure 2:
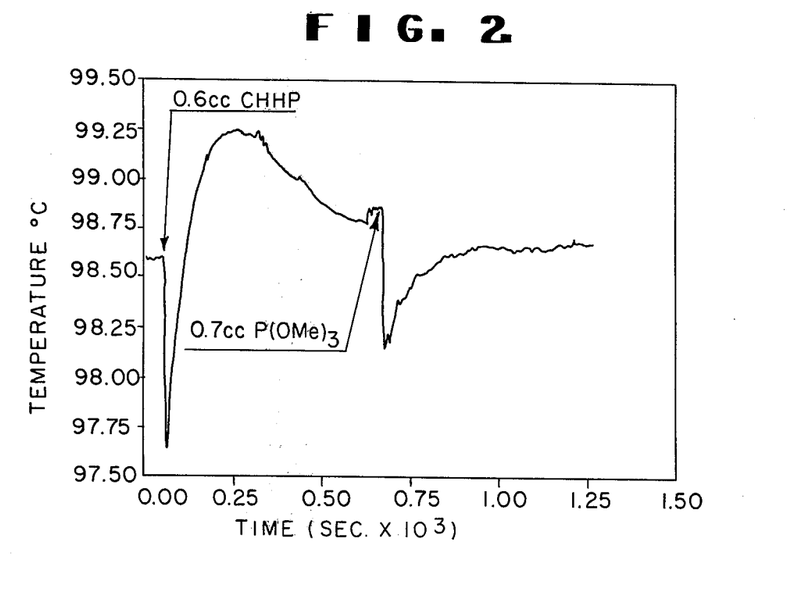

Data for light intensity (I) as a function of time and for temperature (T) as a function of time are shown plotted in FIGS. 1 and 2, respectively.

Discussion of FIGS. 1 and 2

The decomposition of CHHP produces chemiluminescence, and the intensity of the light at any time is a direct measure of the rate of decomposition. The intensity/time curve in FIG. 1 shows that CHHP decomposed rapidly for 2–3 minutes after it was injected in Example 1, after which the rate dropped off and was essentially zero after ten minutes.

Trimethyl phosphite reacts rapidly and exothermically with CHHP according to the following equation:

$$C_6H_{11}OOH + P(OMe)_3 \rightarrow C_6H_{11}OH + OP(OMe)_3.$$

In a time/temperature plot the height of the exotherm ($\Delta T$) corresponding to the trimethyl phosphite/CHHP quench is therefore a direct measure of the amount of CHHP present and is inversely related to the effectiveness of the catalyst being used. A catalyst can be evaluated by comparing its $\Delta T_{quench}$ with the value of $\Delta T$ produced in the absence of a catalyst. If there is little or no CHHP present when the trimethyl phosphite is added, the value of $\Delta T_{quench}$ can be negative. The reason is that the trimethyl phosphite, which is at room temperature when it is injected, can have a cooling effect when added to the system at 99°.

FIG. 2 shows that the temperature of the system dropped abruptly about 1° when the relatively cool solution of CHHP and diethyl ether was added, rose abruptly because of the exothermic decomposition reaction, and then slowly decreased until the time when the trimethyl phosphite was added. A $\Delta T$ of $-0.7°$ (i.e., an endotherm) was recorded upon this addition. Comparison with a $\Delta T$ of $-0.9°$ in a blank system containing no CHHP showed that substantially all the CHHP was decomposed by the Co(BPI)$_2$ in ten minutes at about 99°. With reference back to FIG. 1, it can now be seen that the rate of decomposition of CHHP dropped essentially to zero by the time the trimethyl phosphite was added because there was essentially no more CHHP to decompose.

Control Experiment with Cobalt 2-Ethylhexanoate

The procedure of Example 1 was repeated, except that 10 ppm of cobalt 2-ethylhexanoate was used instead of 10 ppm of Co(BPI)$_2$. A flocculent precipitate was found in the reactor after the run. After filtration the solution was found to contain less than 0.1 ppm of cobalt, which finding indicated that essentially all the cobalt had precipitated.

Figure 3:
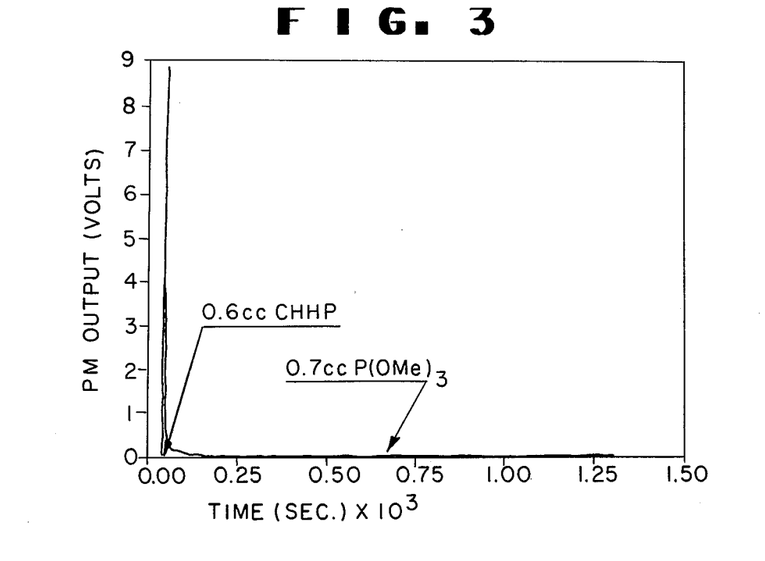
Figure 4:
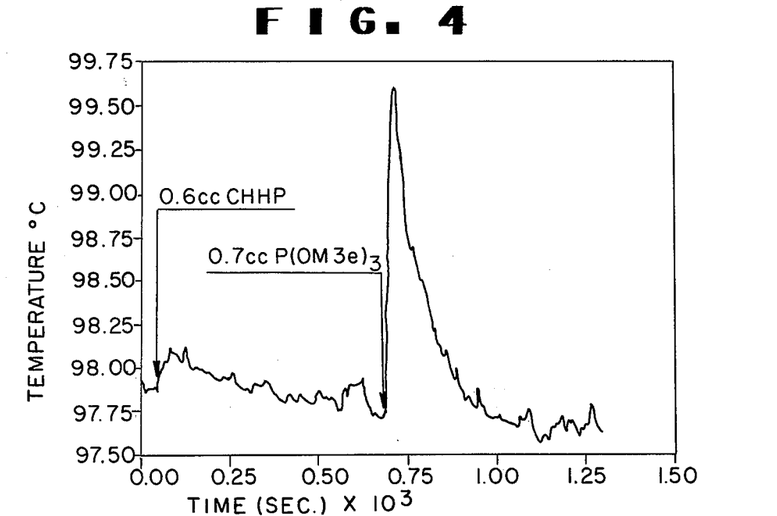

Light intensity/time data and temperature/time data are shown plotted in FIGS. 3 and 4, respectively. FIG. 3 shows that the catalyst had lost most of its activity within 20 seconds following the injection of CHHP. FIG. 4 shows that the trimethyl phosphite quench produced an exotherm of 1.9°. The extent of CHHP decomposition can be calculated from this and other information by the following equation ("cat"=catalyst):

$$\% \ CHHP \ \text{decomposed} = \frac{\Delta T_{no\ cat} - \Delta T_{cat}}{\Delta T_{no\ cat} - \Delta T_{no\ CHHP}} \times 100$$

The value of $\Delta T_{no\ cat}$, determined from a run similar to Example 1 but with no catalyst present, is 5.2°. From the present experiment, the value of $\Delta T_{cat}$ is 1.9°, and from the discussion of FIGS. 1 and 2 the value of $\Delta T_{no\ CHHP}$ is $-0.9°$. Substituting these values in the foregoing equation shows that only about 54% of the CHHP charged was decomposed in the control run with cobalt 2-ethylhexanoate catalyst, compared with essentially complete decomposition when Co(BPI)$_2$ was used. (Calculation via the foregoing equation gives a value of 97% CHHP decomposed with Co(BPI)$_2$.)

The foregoing data show that Co(BPI)$_2$ is a better catalyst than cobalt 2-ethylhexanoate for the decomposition of CHHP and is less decomposed itself in the process.

EXAMPLE 2

Procedure

Figure 5:
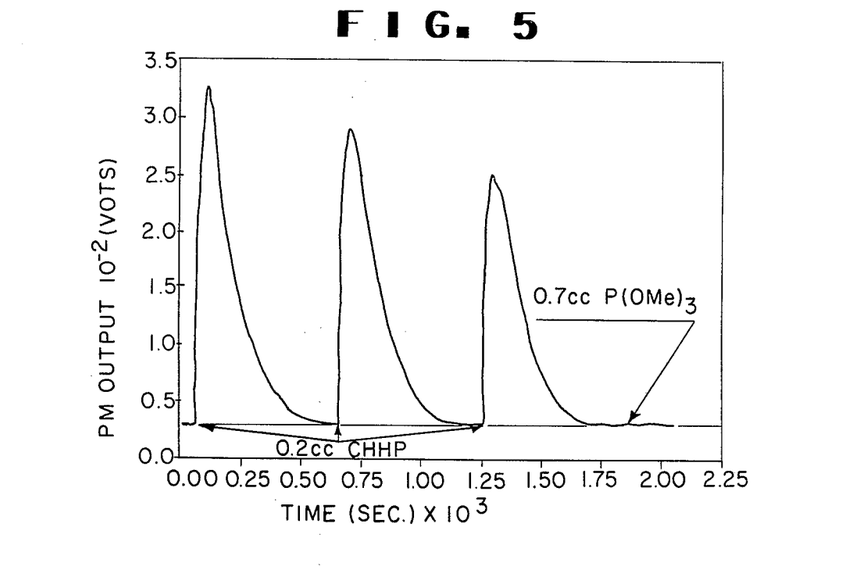
Figure 6:
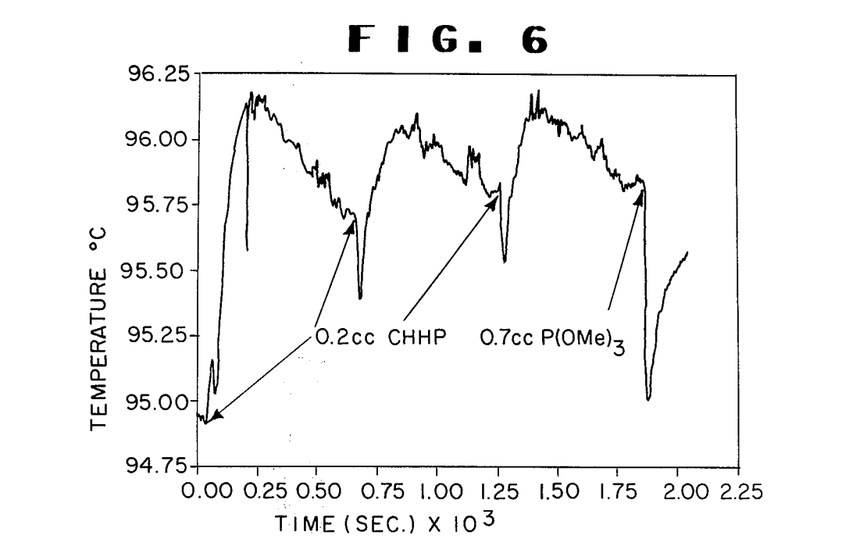

Example 1 was repeated, except that the CHHP solution was added in three 0.2-cc portions at 10-minute intervals, rather than all at once. In addition the reaction temperature was about 96°, and the reaction was carried out in an atmosphere of nitrogen; however, these two variations do not affect the results significantly. The trimethyl phosphite was added 10 minutes after the third and last injection of CHHP. The final solution was found to contain 4.8 ppm of cobalt. The data plotted in FIGS. 5 and 6 show that the CHHP added in each injection decomposed completely in the presence of the Co(BPI)$_2$ catalyst, with little or no loss of catalytic activity throughout the experiment. The $\Delta T_{quench}$ of $-0.8°$, showed in FIG. 6, confirms this result.

Control Experiment with Cobalt 2-Ethylhexanoate

Figure 7:
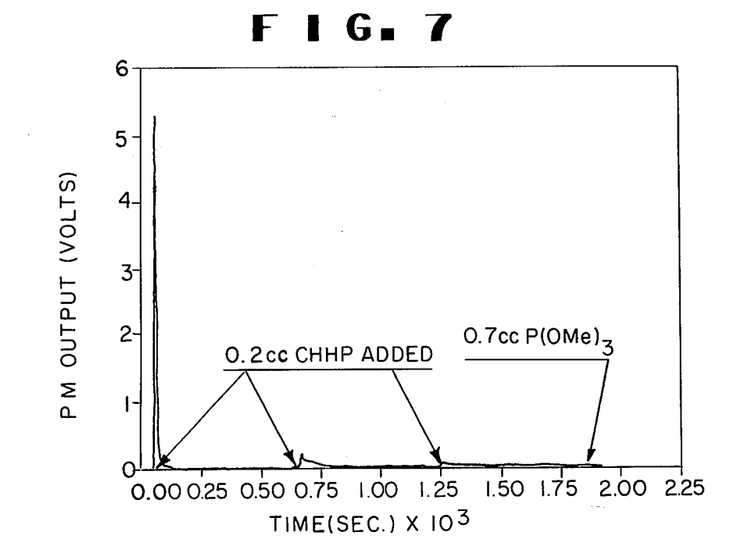
Figure 8:
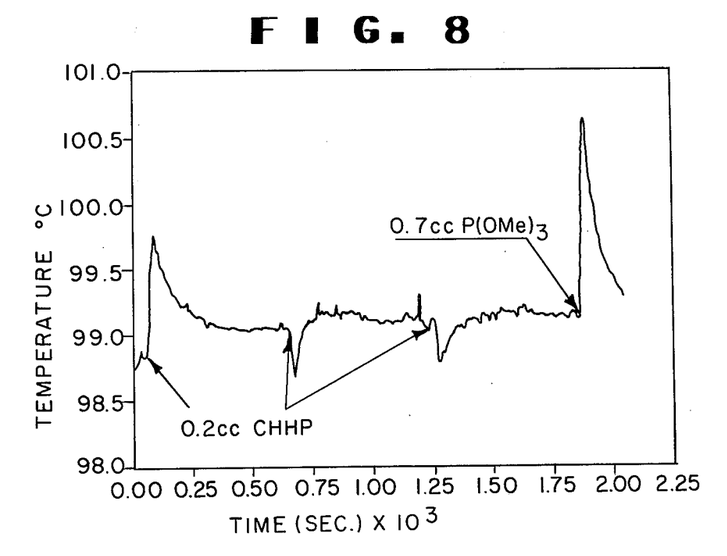

Example 2 was repeated at 99° with cobalt 2-ethylhexanoate as catalyst in place of Co(BPI)$_2$. A flocculent precipitate was formed, and only 2.0 ppm of cobalt was found in the final solution. The data plotted in FIGS. 7 and 8 show that the cobalt 2-ethylhexanoate catalyst became markedly less effective with each successive injection of CHHP. The $\Delta T_{quench}$ of 1.45° shown in FIG. 8 indicates that only 62% of all the CHHP injected was decomposed in the overall run.

EXAMPLES 3-6

By substantially the method of Example 1, other cobalt-containing catalysts of the invention were used in the decomposition of CHHP. These runs were carried out at temperatures of 95°-99°. The results are shown in Table 1. Data for Example 1 are included for comparison. Also included for comparison are data for cobalt 2-ethylhexanoate.

TABLE 1

| Example | Catalyst* | $\Delta T_{Quench}$ °C. | % CHHP Decomposition | ppm Co in Final Soln. |
|---|---|---|---|---|
| 3 | Co(4-MeBPI)$_2$ | −0.5 | 93 | 3.0 |
| 4 | Co(5-MeBPI)$_2$ | −0.45 | 93 | 2.2 |
| 5 | Co(IQBPI)$_2$ | −0.35 | 91 | 1.0 |
| 6 | Co(3-MeBPI)$_2$ | −0.65 | 96 | 2.9 |
| 1 | Co(BPI)$_2$ | −0.7 | 97 | 2.2 |
|   | Co(oct)$_2$ | +1.9 | 54 | <0.1 |

*Co(4-MeBPI)$_2$: Cobalt (II) derivative of 1,3-bis(4-methylpyridylimino)isoindoline
Co(5-MeBPI)$_2$: Cobalt (II) derivative of 1,3-bis(5-methylpyridylimino)isoindoline
CO(IQBPI)$_2$: Cobalt (II) derivative of 1,3-bis(1-isoquinolylimino)isoindoline
Co(3-MeBPI)$_2$: Cobalt (II) derivative of 1,3-bis(3-methylpyridylimino)isoindoline
Co(BPI)$_2$: Cobalt (II) derivative of 1,3-bis(pyridylimino)isoindoline
Co(oct)$_2$: Cobalt (II) 2-ethylhexanoate (cobalt octoate)

EXAMPLE 7

This example is to show that the well-known K+A products conventionally obtained from the decomposition of CHHP are also obtained in the process of the present invention.

The reaction vessel was of the same type as that of Example 1, except that it had a volume of about 125 ml and could be used at pressures up to about 300 psi (2070 kPa). It was charged with 25 cc of cyclohexane, 0.0414 g of Co(BPI)$_2$, 0.2028 g (1.748 mmol) of CHHP, and 0.2209 g of chlorobenzene. The chlorobenzene was present as an internal standard for analysis by gas chromatography (gc). The reactor was sealed, and the reaction mixture was heated at 151°-154° for 15 minutes with stirring to obtain a product mixture which when analyzed by gc showed the presence of 0.313 mmol of cyclohexanone (K) and 1.565 mmol of cyclohexanol (A). The mole ratio (K+A)/CHHP was 1.07, corresponding to a practically complete conversion of the cyclic C$_6$ moiety of CHHP to K and A. The 7% above 100% conversion corresponds to extra K and/or A formed by reaction of oxygen with the cyclohexane. The oxygen was present as a component of air and as a by-product of CHHP decomposition.

The catalyst concentration in this example was 191 ppm of cobalt. This is much higher than what is required, especially at a relatively high temperature of 150°. Although there is no point in using higher catalyst concentrations than about 0.1-30 ppm of cobalt, there also is no harm in doing so; i.e., the course of the decomposition reaction will not be changed.

EXAMPLES 8-13

Using a procedure similar to that described in Example 1, with differences noted below, various catalysts of the invention were used to decompose CHHP. Other details of these examples are given in Table 2. In Examples 11-13 a reactor similar to that described in Example 7 was used; 25 ml of cyclohexane was charged; the catalyst was added as an aliquot of a stock solution in benzene which was prepared so that 0.5 ml of solution gave 5 ppm of metal in the reaction mixture; DBA was charged as an 0.1 M solution in benzene; CHHP was injected as a 50% solution in cyclohexane; and the mixture was heated in a sand bath. The values of $\Delta T_{no\ cat}$ and $\Delta T_{no\ CHHP}$ for these experiments varied among the several examples. These variations were taken into account in calculating the values of % CHHP decomposed.

TABLE 2

| Ex. | Catalyst | ppm | Temp | $\Delta T_{Quench}$ °C. | % CHHP Decomposed |
|---|---|---|---|---|---|
| 8 | Co(BPI)OH | 10 | 95° | 3.5 | 34 |
| 9 | Mn(BPI)$_2$ | 10 | 95° | −0.2 | 89 |
| 10 | Fe(BPI)$_2$ | 10 | 95° | −0.65 | 96 |
| 11 | Co(345MeBPI)$_2$ | 10 | 100° | 0.45 | 83 |
| 12 | Fe(3MeBPI)$_2$ | 10 | 100° | −0.3 | 100 |
| 13 | Mn(3MeBPI)$_2$ | 10 | 100° | 6.7 | 21 |

EXAMPLES 14–26

By using a procedure similar to that described in Example 1 with exceptions noted below and a reactor similar to that described in Example 7, catalysts of the invention were used to decompose CHHP in an oxidation mixture (tails) from plant operation. The oxidation mixture contained cyclohexane, cyclohexanol, cyclohexanone, and impurities from the plant process. The catalyst was charged at the reaction temperature which was 100° and was the last component of the reaction mixture to be charged. Other details are summarized in Table 3. In Examples 14–16 the reactor was charged with 25 ml of tails and about 8.5 mg of DBA as a 0.1 M solution in chlorobenzene and heated to 100°. There was added 0.5 ml of a solution of catalyst in chlorobenzene, the solution having been made up so that 0.5 ml would give 5 ppm of metal in the reaction mixture. In Examples 17–26 benzene was used as the solvent for DBA and the catalyst. In addition, after the reaction temperature was reached but 0.5 minutes before the catalyst was added, 0.5 ml of a 50% solution of CHHP in benzene was added. This added CHHP comprised about 1% of the reaction mixture. A control experiment using the procedure of Examples 14–16 was also run.

TABLE 3

| Example | Catalyst | $\Delta T_{Quench}$ °C. | % CHHP Decomposed |
|---|---|---|---|
| 14 | Fe(BPI)$_2$ | 4.3 | 21 |
| 15 | Co(BPI)OAc | 2.5 | 50 |
| 16 | Mn(BPI)$_2$ | 4.1 | 24 |
| 17 | Co(3MeBPI)$_2$:Mn(3MeBPI)$_2$ (5.4:4.6) | 4.7 | 54 |
| 18 | Co(3MeBPI)$_2$:Fe(3MeBPI)$_2$ (6:4) | 4.3 | 65 |
| 19 | Co(3MeBPI)$_2$ | 3.8 | 69 |
| 20 | Co(3MeBPI)$_2$ | 6.5 | 48 |
| 21 | Fe(3MeBPI)$_2$ | 10.6 | 15 |
| 22 | Co(3MeBPI)$_2$:Fe(3MeBPI)$_2$ (7:3) | 6.6 | 47 |
| 23 | Mn(3MeBPI)$_2$ | 9.0 | 12 |
| 24 | Co(oct)$_2$:Fe(3MeBPI)$_2$ (2:1)** | 2.6 | 79 |
| 25 | Co(oct)$_2$:Co(3MeBPI)$_2$ (2:1)** | 7.3 | 40 |
| 26 | Co(BPI)$_2$ | 8.5 | 31 |
| Control | Co(oct)$_2$ | 4.6 | 13 |

*Ratios for two-component catalysts are molar.
**Components were physically mixed.

EXAMPLES 27–29

In situ synthesis

A reaction vessel similar to that described in Example 7 was charged with 25 ml of cyclohexane, 8.6 mg DBA, and sufficient Co(oct)$_2$ to give 10 ppm of Co by weight in the resulting mixture. The Co(oct)$_2$ was supplied as 0.1 ml of a stock solution containing 0.016 g of Co(oct)$_2$ in 1 cc cyclohexane. The mixture was then heated to approximately 100° with stirring, and 0.5 cc of 50% CHHP by volume in cyclohexane was added. Ten minutes later 0.3 cc trimethyl phosphite was added to determine the amount of unreacted CHHP. A temperature rise of 5.2° indicated that about 60% of the CHHP had not reacted.

In a subsequent experiment (Example 27) where 1.1 mg of free 1,3-bis(3-methylpyridylimino)isoindoline (H3MeBPI) was added to the Co(oct)$_2$ before heating, the exotherm was only 0.4°. Table 4 shows that increasing the ligand-to-cobalt ratio of 2:1 results in an endotherm of −0.25°, indicating substantially complete CHHP decomposition. Further increases in ligand-to-cobalt ratio are not necessary as shown by the results of Example 29 in the table.

Visual observations of color changes indicate that Co(oct)$_2$ reacts practically instantaneously on mixing with H3MeBPI to give a composition which contains Co(3MeBPI), which are responsible for the improved catalytic performance. Experiments with H3MeBPI without cobalt show that the free isoindoline compound is not by itself effective as a catalyst.

TABLE 4

Tests of Catalysts Prepared by Mixing Co(oct)$_2$ With H3MeBPI

| Example | (ppm) Co Conc | Mole Ratio Ligand:Co | (°C.) ΔT (quench) |
|---|---|---|---|
| Control | 10 | 0 | 5.2 |
| 27 | 10 | 1:1 | 0.4 |
| 28 | 10 | 2:1 | −0.25 |
| 29 | 10 | 2.5:1 | −0.25 |

EXAMPLE 30

The apparatus used in this example was similar to that described for Example 7 and was equipped with a pressure flow controller to permit electronic monitoring of the reactor pressure and feed of O$_2$ gas using a mass flow controller.

The reactor was charged with 2.0 mg of Co(3MeBPI)$_2$ (to give 7 ppm Co by weight), 30 cc of cyclohexane, and 8.6 mg of DBA. The temperature was raised to 135° and O$_2$ was fed into the reactor until the pressure had increased by about 15 psi (103 kPa). The observation of chemiluminescence and the fact that a steady feed of O$_2$ was required to maintain constant pressure showed that the oxidation was proceeding at this low temperature. After about 65 minutes when the O$_2$ consumption indicated that about 5% of the cyclohexane was converted to products, the reactor was cooled in ice water and then opened to give a clear yellow liquid containing precipitated solids.

GC analysis of the liquid showed that K and A were the major products, representing 89% of the peak area (for peaks eluting between 3.0 and 20.0 minutes), and with a K/A area ratio of 0.42.

In order to render all of the products volatile (including such normally nonvolatile products as adipic acid), a portion of the liquid product was reduced with lithium aluminum hydride (LAH). This had the effect of reducing ketones, aldehydes, esters, and acids to volatile alcohols (e.g. adipic acid to 1,6-hexanediol). To 0.1 g of LAH in a 50 ml round bottom flask equipped with magnetic stirring bar and reflux condenser was added 5 ml of liquid product. After the reaction mixture was stirred and refluxed for about 8 hours, the flask was cooled to room temperature and 2 ml of a solution of 90% isopropyl alcohol and 10% H$_2$O carefully added to destroy any remaining LAH. The sample was then quantitatively transferred to a 10 ml volumetric flask and tetrahydrofuran added to give a total volume of 10.0 ml. Aluminum containing solids were allowed to settle and a portion of the clear supernatant liquid taken for GC analysis.

The gas chromatogram showed that A (derived from A, K, CHHP or other cyclohexyl peroxides, and cyclohexyl esters) represented 90.1% on a mole basis, 1,2-cyclohexanediol 0.4%, and 1,6-hexanediol 1.6%. This low temperature oxidation shows a high yield of useful products, when compared with conventional oxidations using $Co(oct)_2$ at 165°.

EXAMPLE 31

Reactions for this example were carried out in a continuous semiworks consisting of an oxidizer, a CHHP reactor, a dry stripper, and a wet stripper—designed to simulate a large scale commercial process. The oxidizer was of the sieve-tray design described in U.S. Pat. No. 3,530,185, and was fed at the top with catalyst solution, fresh cyclohexane, and recycled cyclohexane from which water has been allowed to separate. The CHHP reactor was a smaller sieve-tray reactor equipped with catalyst solution feed at the top and gas feed at the bottom. The strippers remove unreacted cyclohexane for recycle to the oxidizer, the wet stripper removing the last of the cyclohexane as an azeotrope with water. The product produced is referred to hereafter as whole crude KA (WCKA). The conditions used are summarized in Table 5. This example shows the effect of using the cobalt (II) derivative of 1,3-bis(4-t-butyl-2-pyridylimino)isoindoline [$Co(4tBuBPI)_2$] as a catalyst in a low temperature CHHP decomposition in the presence of molecular oxygen. Comparison may be made with the Control, in which $Co(oct)_2$ is used in both the oxidizer and high-temperature CHHP reactor.

Under the conditions of this example, there was obtained oxidation of approximately one mole of additional cyclohexane per mole of CHHP decomposed, thus increasing the overall conversion above that in the oxidizer by about 15%. This represents a valuable increase in plant production capacity.

Table 6 shows the results of GC analysis of WCKA samples produced in these examples, after LAH reduction. The reduction procedure was similar to that described in Example 30, except that 250 mg of sample was reduced in 5 ml tetrahydrofuran. The butanol, pentanol, and hexanol listed in Table 6 largely represent reduced monobasic acids, since butanol and pentanol are largely recycled and hexanol is not directly produced in the oxidation. The 1,6-hexanediol comes largely from adipic acid, although caprolactone, hydroxycaproic acid, and other precursors made small contributions. Both 1,6-hexanediol and 1,2-cyclohexanediol represent adipic acid potential, since either they or their precursors can be oxidized to adipic acid by well known procedures using nitric acid. It can be seen in Table 6 that the low temperature CHHP decomposition in the presence of oxygen using $Co(4tBuBPI)_2$ gives higher yields of A (after reduction) or of adipic precursors, when compared with the Control.

TABLE 5

| Cyclohexane Oxidation Semiworks Run Conditions | | |
|---|---|---|
| | Control | Example 31 |
| Air Oxidizer | | |
| Cyclohexane feed (ml/min) | 260 | 260 |
| Air Feed (std liters/min) | 6.0 | 6.0 |

TABLE 5-continued

| Cyclohexane Oxidation Semiworks Run Conditions | | |
|---|---|---|
| | Control | Example 31 |
| $N_2$ feed (std liters/min) | 2.0 | 2.0 |
| Mean Temperature (°C.) | 166 | 166 |
| Catalyst and concentration (ppm) | 0.1 Co(oct)$_2$ | 0.1 Co(oct)$_2$ |
| Conversion (%) | 4.2 | 4.1 |
| CHHP Reactor | | |
| Temperature | 162 | 115 |
| Catalyst concentration (ppm) | 1.0 Co(oct)$_2$ | 1.1 Co(4tBuBPI)$_2$ |
| Gas feed (std liters/min of 4% $O_2$ in $N_2$) | — | 7 |

TABLE 6

| GC Analyses of WCKA Samples After LAH Reduction | | |
|---|---|---|
| | Mole Percentages | |
| Component | Control | Example 31 |
| butanol | 1.3 | 0.9 |
| pentanol | 4.1 | 3.4 |
| hexanol | 1.0 | 0.7 |
| A | 88.3 | 89.8 |
| 1,4-butanediol | 0.5 | 0.4 |
| 1,2-cyclohexanediol(1,2-C) | 0.3 | 0.2 |
| 1,5-pentanediol | 1.0 | 1.0 |
| 1,6-hexanediol(1,6-H) | 2.4 | 2.5 |
| A + 1,2-C + 1,6-H | 91.0 | 92.5 |

EXAMPLES 32 AND 33

The reaction vessel used in this example was similar to that used in Example 7.

In an atmosphere of air, the reactor was charged with 20 cc of cyclohexane and 0.042 ml of a solution of $Co(3MeBPI)_2$ in dichloromethane containing 0.056 weight percent Co. The system was pressured to about 20 psig (1.4 kg/cm$^2$) with air in Example 32, to about 60 psig (4.2 kg/cm$^2$) with air in Example 33, and the reactor sealed. The system was heated to 110° with stirring and a mixture of 0.2073 g of CHHP and 0.0849 g of diphenyl ether (as an internal standard for gc analysis) was injected in Example 32 and 0.2114 g of CHHP and 0.0887 g of diphenyl ether in Example 33. The resulting mixture was heated with stirring at 110° for 15 minutes and then cooled, following which it was analyzed by gc.

A control experiment, in which no molecular oxygen was present at the start, was run by substantially the foregoing procedure, except that after the cyclohexane and the catalyst solution were charged, the reactor was evacuated three times to about 100 mm of Hg and pressure with nitrogen to about 20 psig (1.4 kg/cm$^2$) after each evacuation; after the third admission of nitrogen the system was bled down to atmospheric pressure.

| Example | Mole ratio $O_2$/CHHP | a Mmol CHHP charged | b | c | d | b + c − (a − d) |
|---|---|---|---|---|---|---|
| | | | \multicolumn{3}{c|}{Mmol found} | |
| | | | K | A | CHHP | |
| Control | 0 | 1.78 | 0.57 | 1.68 | 0 | 0.47 |
| 32 | 0.9 | 1.79 | 0.97 | 2.65 | 0.15 | 1.98 |
| 33 | 2.7 | 1.82 | 1.10 | 2.52 | 0.29 | 2.09 |

The results of Examples 42 and 43 show that the beneficial effect of oxygen addition on cyclohexane participation is realized at a relatively low $O_2$/CHHP ratio (0.9) by using Co(3MeBPI)$_2$ as catalyst and operating at 110°.

We claim:

1. In a process for producing a mixture containing cyclohexanol and cyclohexanone wherein cyclohexane is oxidized in air to provide a reaction mixture containing cyclohexyl hydroperoxide and the cyclohexyl hydroperoxide is decomposed in the presence of starting cyclohexane to provide a mixture containing cyclohexanol and cyclohexanone, the improvement comprising (1) conducting the oxidation step by contacting cyclohexane with air at a temperature of from about 120°–160° C. in the presence of a catalytic amount of catalyst composition consisting essentially of at least one transition metal complex having the structural formula wherein the primary ligand is the entity in brackets;

M is Co, Mn or Fe;

$R^1$, $R^2$, $R^3$, $R^4$, $R^5$, and $R^6$ are independently hydrogen, lower alkyl, lower alkoxyalkyl, phenyl, benzyl, or phenethyl or any two adjacent members of $R^1$ through $R^6$ are jointly four CH entities of a benzene ring fused to the pyridine ring;

$R^7$, $R^8$, $R^9$ and $R^{10}$ are independently hydrogen, lower alkyl or lower alkoxyalkyl or any two adjacent members of $R^7$ through $R^{10}$ can jointly be four CH entities of a benzene ring fused to the benzene ring of the isoindoline moiety;

X is an ancillary anionic ligand;

n is 1 or 2;

p is 0, 1 or 2, provided that n+p is 2 or 3;

with the proviso that when there are two primary ligands the values of $R^1$ through $R^{10}$ can be different for each ligand and when there are two ancillary anionic ligands the value of X can be different;

and/or (2) conducting the decomposition step by contacting a reaction mixture containing cyclohexane and from about 0.1 to about 10% by weight of cyclohexyl hydroperoxide with a catalytic amount of said catalyst composition at a temperature of from about 80°–160° C., optionally in the presence of molecular oxygen.

2. The process of claim 1 wherein $R^7$ through $R^{10}$ are independently hydrogen or lower alkyl and p is 0 or 1.

3. The process of claim 2 wherein the catalyst is present during the oxidation step.

4. The process of claim 3 wherein the temperature is from about 140°–150° C.

5. The process of claim 4 wherein the catalyst is present in an amount to provide from about 0.1 to about 10 ppm of metal by weight.

6. The process of claim 2 wherein the catalyst is present during the decomposition step and the contacting is done in the absence of molecular oxygen.

7. The process of claim 6 wherein the temperature is from about 100°–130° C.

8. The process of claim 7 wherein the catalyst is present in an amount to provide from about 0.1 to about 30 ppm of metal by weight.

9. The process of claim 8 wherein the catalyst is present in an amount to provide from about 0.1 to 5 ppm of metal by weight.

10. The process of claim 9 wherein the contact time is from about 5 to about 30 minutes.

11. The process of claim 2 wherein the catalyst is present during the decomposition step and the contacting is done in the presence of molecular oxygen, said molecular oxygen being present in a mole ratio of oxygen to cyclohexyl hydroperoxide of about 0.1 or greater.

12. The process of claim 11 wherein the temperature is from about 80°–140° C.

13. The process of claim 12 wherein the temperature is from about 100°–120° C.

14. The process of claim 13 wherein molecular oxygen is present in a mole ratio of oxygen to cyclohexyl hydroperoxide of from about 0.1 to about 10.

15. The process of claim 14 wherein the mole ratio of oxygen to cyclohexyl hydroperoxide is from about 0.5 to about 3.0.

16. The process of claim 15 wherein the reaction mixture contains from about 0.5 to about 3% of cyclohexyl hydroperoxide by weight.

17. The process of claims 5, 10, or 16 wherein M is Co.

18. The process of claim 17 wherein $R^1$, $R^2$, $R^3$, $R^4$, $R^5$ and $R^6$ are independently hydrogen, methyl or t-butyl.

19. The process of claim 18 wherein any two of $R^1$, $R^2$ and $R^3$ and any two of $R^4$, $R^5$ and $R^6$ are hydrogen, p is 0, n is 2, and $R^7$ through $R^{10}$ are hydrogen.

20. The process of claim 19 wherein any one of $R^1$, $R^2$ and $R^3$ and any one of $R^4$, $R^5$ and $R^6$ are methyl.

21. The process of claim 20 wherein $R^1$ and $R^4$ are methyl.

22. The process of claim 19 wherein $R^2$ and $R^5$ are t-butyl.

23. The process of claim 18 wherein $R^1$ through $R^{10}$ are hydrogen, p is 0, and n is 2.

* * * * *